United States Patent
Shiomi et al.

(10) Patent No.: US 7,392,178 B2
(45) Date of Patent: Jun. 24, 2008

(54) CHAOS THEORETICAL DIAGNOSIS SENSITIZER

(75) Inventors: Kakuichi Shiomi, Tokyo (JP); Naritomo Meguro, Kanagawa (JP); Tomoya Maruyama, Tokyo (JP)

(73) Assignees: Electronic Navigation Research Institute, An Independent Administration Institution, Tokyo (JP); Mitsubishi Space Software Co., Ltd., Tokyo (JP)

( * ) Notice: Subject to any disclaimer, the term of this patent is extended or adjusted under 35 U.S.C. 154(b) by 481 days.

(21) Appl. No.: 10/508,785

(22) PCT Filed: Feb. 26, 2003

(86) PCT No.: PCT/JP03/02159
§ 371 (c)(1),
(2), (4) Date: Sep. 23, 2004

(87) PCT Pub. No.: WO03/081575
PCT Pub. Date: Oct. 2, 2003

(65) Prior Publication Data
US 2005/0108014 A1 May 19, 2005

(30) Foreign Application Priority Data
Mar. 25, 2002 (JP) ............................. 2002-082734

(51) Int. Cl.
*G10L 19/14* (2006.01)
(52) U.S. Cl. .................. 704/211; 704/249; 704/254
(58) Field of Classification Search ............... 704/231, 704/235, 243, 244, 245, 270.1, 270, 276, 704/254, 211, 246, 247, 248, 249, 250
See application file for complete search history.

(56) References Cited

U.S. PATENT DOCUMENTS 5,640,490 A * 6/1997 Hansen et al. ............... 704/254

(Continued)

FOREIGN PATENT DOCUMENTS

JP 8-292788 11/1996

(Continued)

OTHER PUBLICATIONS

Miyashita et al. "An analysis of chaotic properties in phoneme in continuous speech by plural speakers". Intelligent System Symposium, Sep. 2001, pp. 33-36.

(Continued)

*Primary Examiner*—Huyen X. Vo
(74) *Attorney, Agent, or Firm*—Wenderoth, Lind & Ponack, L.L.P.

(57) ABSTRACT

The present invention is a preprocessing apparatus including a voice input apparatus for acquiring an uttered voice, an analog-digital conversion apparatus for converting the acquired uttered voice to digital voice data, and a comparator for selecting voice data, having a level which is equal to or higher than a certain level, from the digital voice data and for outputting the selected voice data. The preprocessing apparatus also includes a voice data cutout apparatus capable of cutting out voice data having a level which is equal to or higher than a certain level output from the comparator, while taking a phoneme as a unit, and a voice data output apparatus for outputting voice data of the phoneme unit output from the voice data cutout apparatus.

5 Claims, 5 Drawing Sheets

U.S. PATENT DOCUMENTS

2004/0243401 A1 12/2004 Shiomi et al.

FOREIGN PATENT DOCUMENTS

| JP | 3151489 | 1/2001 |
| JP | 2003-79602 | 3/2003 |
| WO | 97/34293 | 9/1997 |
| WO | 02/085215 | 10/2002 |

OTHER PUBLICATIONS

Shiomi et al. "Fatigue analysis method based on chaos theory and modeling of human brain function". Information Processing Society of Japan, Mar. 2002, pp. 209-212.

Shiomi et al. "Fatigue analyzer for voiced speech". Information Processing Society of Japan, Mar. 2002, pp. 253-254.

Kakuishi Shiomi et al., "Fatigue analyzer for voiced speech", Information Processing Society of Japan, Dai 64 Zenkoku Taikai Koen Ronbunshu(1), 2002, p. I-253 (along with English translation).

Kanae Miyashita et al., "An analysis of chaotic properties in phoneme in continuous speech by plural speakers", Keisoku Jido Seigyo Gakkai (Neural Network Committee), Dai 11 Intelligent system Symposium, Fuzzy, Artificial Intelligence, Neural Networks and Computational Intelligence, FAN Symposium '01 in Sakai, pp. 33-36 (along with English translation).

* cited by examiner

CHAOS THEORETICAL DIAGNOSIS SENSITIZER

BACKGROUND OF THE INVENTION

1. Field of the Invention

The present invention relates to a preprocessing apparatus connected to an apparatus for diagnosing a psychosomatic state of a voice uttered by a human being, an apparatus for diagnosing the brain function, an apparatus for diagnosing a human factor, an apparatus for diagnosing affinity, an apparatus for diagnosing a vocational aptitude, and soon. The present invention belongs to the field of the medical diagnosis technique.

2. Background of the Related Art

In a conventional chaos theoretical diagnosis system or apparatus using uttered voice, a numerical value is used as a diagnosis subject data. This numeric value can be obtained by mechanically dividing a continuous uttered voice into specific processing unit time intervals, such as voice signals each having a temporal length of one second, calculating the first Lyapunov exponent in each processing unit time interval, and conducting statistical processing such as moving average calculation on the calculated first Lyapunov exponent.

If voice data of the processing unit time interval to be used in the chaos theoretical diagnosis is mechanically cut out from an input voice, then a subtle difference in a cutout point in time exerts influence upon the calculated first Lyapunov exponent and causes variation in the diagnosis value.

For reducing the variation in the diagnosis value, it is necessary to set a time that is sufficiently long as compared with the cut out time. For example, by setting an average time in the range of several tens of seconds to several minutes in the case where the processing unit time is set equal to one second. It is also necessary to calculate a temporal average value from the first Lyapunov exponent calculated in respective processing units, and use the temporal average value as a diagnosis value.

When making a chaos theoretical diagnosis from the uttered voice, for example, a continuous uttered voice ranging over at least several minutes is needed as input data in order to get a high diagnosis precision, such as to reduce an error in diagnosis value to several percents or less.

In addition, in the conventional voice signal processing method, it has been impossible to make a significant diagnosis by using a voice signal taken for an interval of approximately several times as long as the processing unit time, such as a voice signal taken for several seconds in the case where the processing unit time interval is one second.

Even if the processing unit time is made shorter, merely the number of the first Lyapunov exponent that must be calculated increases. For example, if the processing unit time is shortened from one second to 0.1 second, the number of the first Lyapunov exponent that must be calculated increases to ten times. Even if a time interval as long as ten times or more is spent for computation processing, the variation in Lyapunov exponent caused by deviation in a point in time, at which each diagnosis data is cutout, cannot be effectively reduced. It is impossible to make a significant diagnosis by using a voice taken for an interval of several seconds.

In the conventional technique described above, it has become an important problem to clarify a method for reducing the variation in the calculated first Lyapunov exponent caused by a difference in a point of time at which diagnosis data is cut out from voice data used in the chaos theoretical diagnosis. Furthermore, a method for calculating a comparatively highly reliable diagnosis value from comparatively short voice data has become an important problem in the same way.

The present invention has been developed to solve the above-described problems. An object of the present invention is to provide an apparatus that reduces the variation in the first Lyapunov exponent calculated using a chaos theoretical diagnosis by cutting out unit voice data used in the chaos theoretical diagnosis while taking a phoneme as the unit, and that calculates a diagnosis value having a reliability equal to or higher than that obtained by using the conventional technique, on the basis of voice data shorter than that in the case using the conventional technique.

SUMMARY OF THE INVENTION

In order to achieve these objects, the invention according to a first aspect provides a sensitivity enhancement apparatus of chaos theoretical diagnosis that is a preprocessing apparatus connected to a chaos theoretical voice diagnosis apparatus for analyzing an uttered voice by using a chaos theory technique, calculating a Lyapunov exponent, and measuring and evaluating a change state of the calculated Lyapunov exponent. The sensitivity enhancement apparatus includes: a voice input apparatus for acquiring the uttered voice; an analog-digital conversion apparatus for converting the uttered voice acquired by the voice input apparatus to digital voice data; a comparator for selecting voice data having a level which is equal to at least a certain input level, from the digital voice data output from the analog-digital conversion apparatus, and for outputting the voice data thus selected; a voice data cutout apparatus capable of cutting out voice data having a level which is equal to at least a certain input level output from the comparator, while taking a phoneme as a unit; and a voice data output apparatus for outputting voice data of phoneme unit output from the voice data cutout apparatus.

As a result, unit voice data cut out in a phoneme or phoneme sequence form can be output to the chaos theoretical diagnosis apparatus as diagnosis data. Therefore, the variation in the first Lyapunov exponent calculated by using the chaos theoretical diagnosis can be remarkably reduced.

In accordance with a second aspect of the invention, in addition to the configuration according to the first aspect, an internal memory for recording the voice data output from the comparator, a phoneme database for storing phoneme data to be collated with the voice data recorded in the internal memory, and a phoneme collation apparatus for cutting out and outputting only a phoneme that coincides with the phoneme data in the phoneme database are connected between the comparator and the voice data cutout apparatus.

As a result, in addition to the effect of the first aspect, it is possible to grasp the psychosomatic state, brain function, human factor, affinity, and vocational aptitude more accurately, by limiting phoneme data stored in the phoneme database to phoneme data of a specific utterer.

In accordance with a third aspect of the invention, in addition to the configuration according to the first aspect, an internal memory for storing the voice data output from the comparator, a phoneme sequence database for storing phoneme sequence data to be collated with the voice data stored in the internal memory, and a phoneme sequence collation apparatus for cutting out and outputting only a phoneme sequence that coincides with the phoneme sequence data in the phoneme sequence database, are all connected between the comparator and the voice data cutout apparatus.

As a result, in addition to the effect of the first aspect, it is possible to grasp the psychosomatic state, brain function, human factor, affinity, and vocational aptitude more accurately, by limiting phoneme sequence data stored in the phoneme sequence database to phoneme sequence data of a specific utterer.

In accordance with a fourth aspect of the invention, in addition to the configuration according to the first aspect, the voice data cutout apparatus starts voice data cutout from the voice data stored in the internal memory at a moment an utterance of a preset vowel or consonant is started, and finishes the voice data cutout at a moment an utterance of at least one phoneme is finished, and thereby cut outs unit voice data formed of a phoneme or a phoneme sequence.

As a result, in addition to the effect of the first aspect, voice data of one phoneme or more, from the moment the utterance of a vowel or consonant is started, is cut out. Consequently, it becomes possible to output more accurate diagnosis data while taking a phoneme as the unit.

In accordance with a fifth aspect of the invention, in addition to the configuration according to the first aspect, the voice data cutout apparatus includes a phoneme discrimination section for arbitrarily selecting and setting a phoneme or phoneme sequence, and cuts out unit voice data formed of a phoneme or a phoneme sequence that coincides with a specific phoneme or a phoneme sequence set by the phoneme discrimination section, from the voice data stored in the internal memory.

As a result, in addition to the effect of the first aspect, a phoneme sequence arranged regularly such as a daily used phrase can be set to unit voice data, and consequently it becomes possible to eliminate an error caused by a mixed presence of a plurality of irregular phonemes. Therefore, diagnosis data required to obtain a diagnosis value having reproducibility can be obtained in a minute.

In accordance with a sixth aspect of the invention, in addition to the configuration according to the fourth or fifth aspect, the voice data cutout apparatus includes offset providing means capable of providing a cutout start moment and a cutout end moment with an offset value equal to one phoneme or less, and when cutting out unit voice data formed of a phoneme or a phoneme sequence from the voice data stored in the internal memory, the cutout start moment and the cutout end moment can be adjusted by the offset providing means.

As a result, in addition to the effect of the fourth or fifth aspect, it becomes possible to correct an apparatus error by conducting fine adjustment of one phoneme or less and it is ensured to provide more accurate diagnosis data.

DETAILED DESCRIPTION OF THE INVENTION

Hereafter, an embodiment of the present invention will be described with reference to the drawings.

FIGS. 1 to 5 show embodiments of the present invention.

Figure 1:
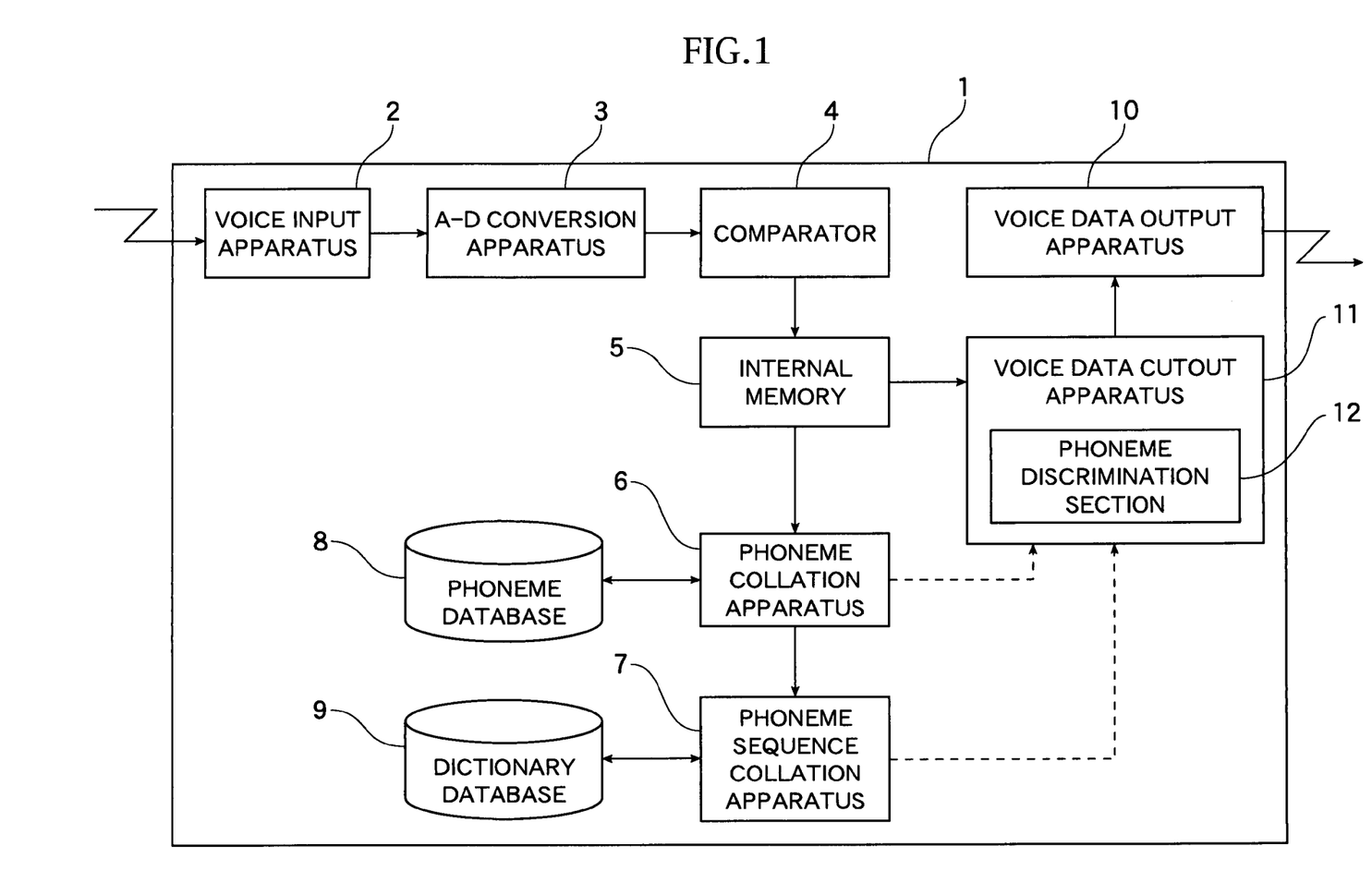
FIG. 1 is a system configuration diagram showing an example of a system configuration of a preprocessing apparatus according to an embodiment of the present invention.

FIG. 1 is a schematic diagram showing a system configuration example of a preprocessing apparatus for chaos theoretical diagnosis according to an embodiment of the present invention.

In FIG. 1, a preprocessing apparatus 1 for chaos theoretical diagnosis (hereafter referred to as "invention apparatus") includes a voice input apparatus 2, an analog-digital conversion apparatus 3, a comparator 4, an internal memory 5, a phoneme collation apparatus 6, a phoneme sequence collation apparatus 7, a phoneme database 8, a dictionary database 9, a voice data cutout apparatus 11 and a voice data output apparatus 10.

The voice input apparatus 2 is a microphone or a tape recorder for acquiring uttered voice of an utterer as analog voice.

The analog-digital conversion apparatus 3 is an apparatus for sampling and quantizing analog voice acquired by the voice input apparatus 2 at a constant sampling frequency and thereby converting the analog voice to digital voice data.

The comparator 4 selects voice data having a level which is equal to or higher than a certain input level, from the digital voice data output from the analog-digital conversion apparatus 3, and outputs the voice data thus selected.

The internal memory 5 is an internal storage apparatus for buffering the voice data output from the comparator 4. The internal memory 5 has a capacity sufficient for the invention apparatus.

The phoneme collation apparatus 6 collates the voice data buffered in the internal memory 5 with a phoneme database 8, which stores phoneme data for each phoneme, and outputs a coincident phoneme as unit phoneme data.

The phoneme sequence collation apparatus 7 collates the voice data as a phoneme sequence, if there are a plurality of phonemes in the voice data, with the dictionary database 9, which stores word dictionary for each phoneme sequence, and outputs a coincident phoneme sequence, and a phoneme sequence width ranging from a voice data start moment to a voice data end moment of the coincident phoneme sequence as second processing data.

The voice data cutout apparatus 11 is an apparatus for acquiring a phoneme or a phoneme sequence as unit voice data. The phoneme or a phoneme sequence is cut out from the internal memory 5 as coincident one and output from the phoneme collation apparatus 6 and the phoneme sequence collation apparatus 7.

The voice data cutout apparatus 11 includes a phoneme discrimination section 12 capable of selecting and setting a phoneme, a phrase to be used in daily conversation, or a phoneme sequence formed of a combination of arbitrary phonemes as unit voice data.

The voice data output apparatus 10 outputs unit voice data as diagnosis data acquired from the internal memory 5 by the voice data cutout apparatus 11. The unit voice data are given to a chaos theoretical diagnosis apparatus following the invention apparatus.

Figure 2:
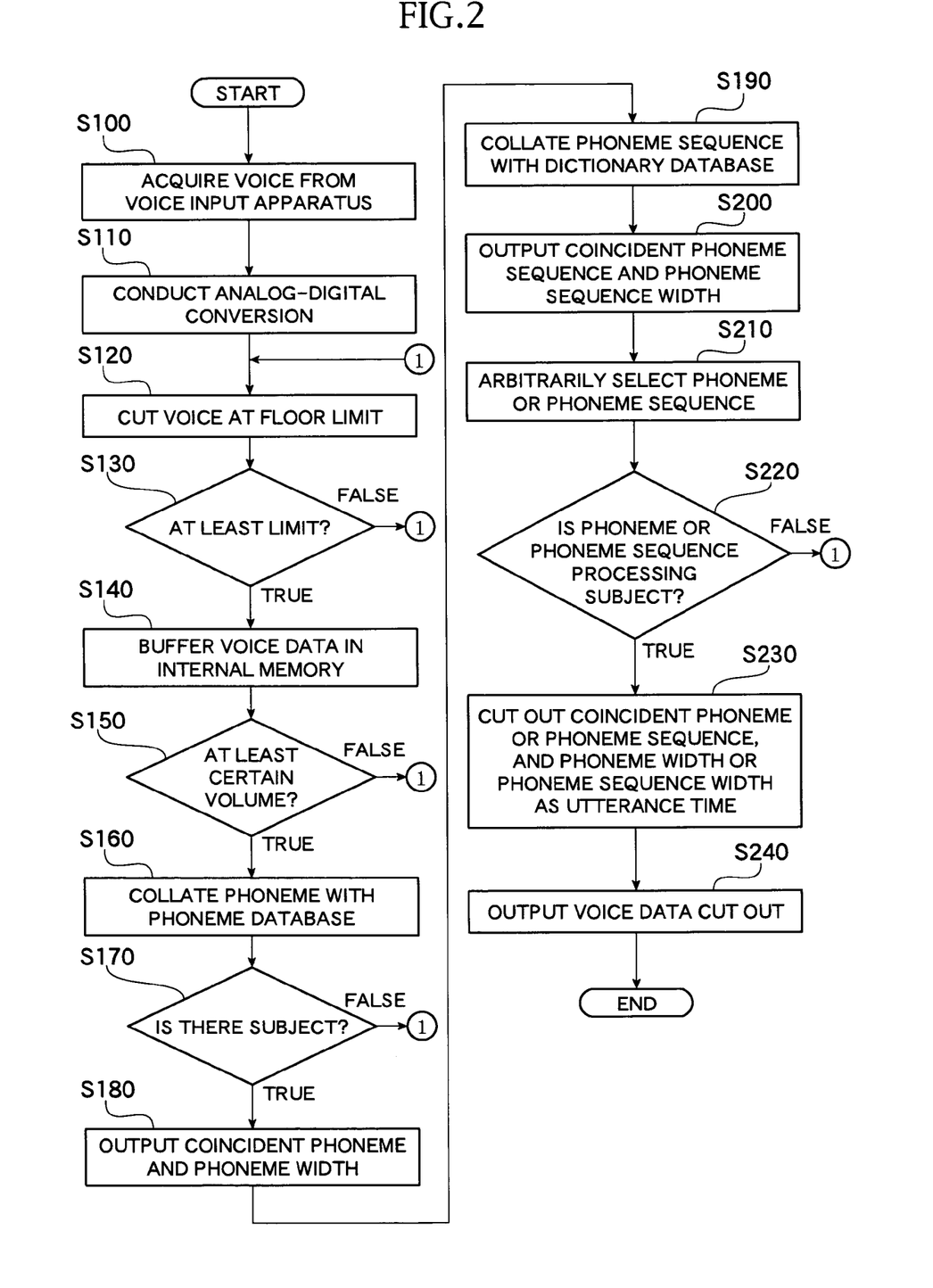
FIG. 2 is a flow chart showing an example of a process flow of a preprocessing apparatus according to the embodiment of the present invention.

FIG. 2 is a flowchart showing a process flow in the invention apparatus.

An uttered voice is acquired as an analog voice by using the voice input apparatus 2 (S100).

In the analog-digital conversion apparatus 3, the voice acquired from the voice input apparatus 2 is sampled and quantized at a constant sampling frequency, and the analog voice is thus converted to digital voice data (S110).

The digital voice data output from the analog-digital conversion apparatus 3 is supplied to the comparator 4 (S120), and only voice data having an input level which is equal to or higher than a certain input level is acquired (S130) and buffered in the internal memory 5 (S140). If the voice data is less than the constant input level, then the voice data is returned to the comparator 4 and the processing is repeated.

If the buffered volume has become at least a certain volume (S150), then voice data in the internal memory 5 is collated in the phoneme collation apparatus with phoneme data stored in the phoneme database 8 (S160). If the buffered volume is less than the certain volume, then the processing is returned to the comparator 4 and repeated.

If there is a phoneme that coincides with a phoneme in the internal memory 5 in the phoneme database 8 (S170), then the phoneme is output from the internal memory 5 (S180). If there is not a coincident phoneme, then the processing is returned to the comparator 4 and repeated.

If there are a plurality of phonemes, then voice data regarded as a phoneme sequence is collated in the phoneme sequence collation apparatus with word dictionary data stored in the dictionary database 9 (S190).

If there is a phoneme sequence that is coincident with a phoneme sequence stored in the dictionary database 9, then a range between a moment at which utterance of the coincident phoneme sequence is started and a moment at which the utterance is finished is set as a cutout range, and a phoneme sequence contained in the range is output (S200).

In the phoneme discrimination section 12 in the voice data cutout apparatus 11, a diagnosing person arbitrarily selects a phoneme or a phoneme sequence to be used as diagnosis data, in advance (S210).

If a phoneme or a phoneme sequence output from the phoneme collation apparatus 6 or the phoneme sequence collation apparatus 7 coincides the arbitrarily selected phoneme or phoneme sequence (S220), then the voice data cutout apparatus 11 cuts out the coincident phoneme or phoneme sequence as unit voice data from the internal memory 5 (S230). If there is no coincident phoneme or phoneme sequence, then the processing is returned to the comparator 4 and repeated.

The voice data output apparatus 10 acquires this unit voice data and outputs the unit voice data to the chaos theoretical diagnosis apparatus following the invention apparatus as diagnosis data (S240).

Means shown in the embodiment are only divided logically in function, but they may form the same region physically or substantially.

Figure 3:
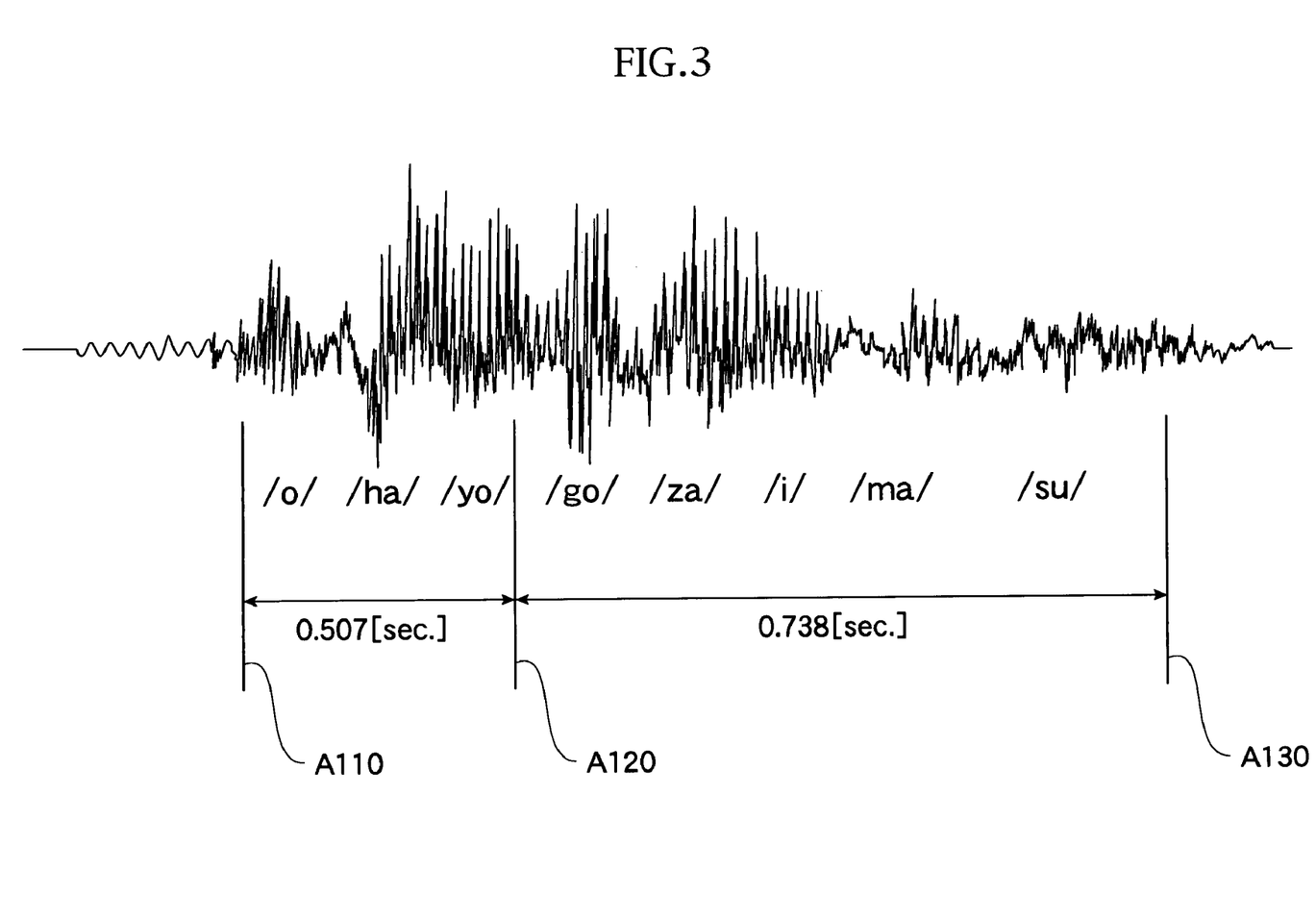
FIG. 3 is a diagram showing a concept of acquiring a phoneme and an utterance time from voice data in a preprocessing apparatus according to the embodiment of the present invention.
Figure 4:
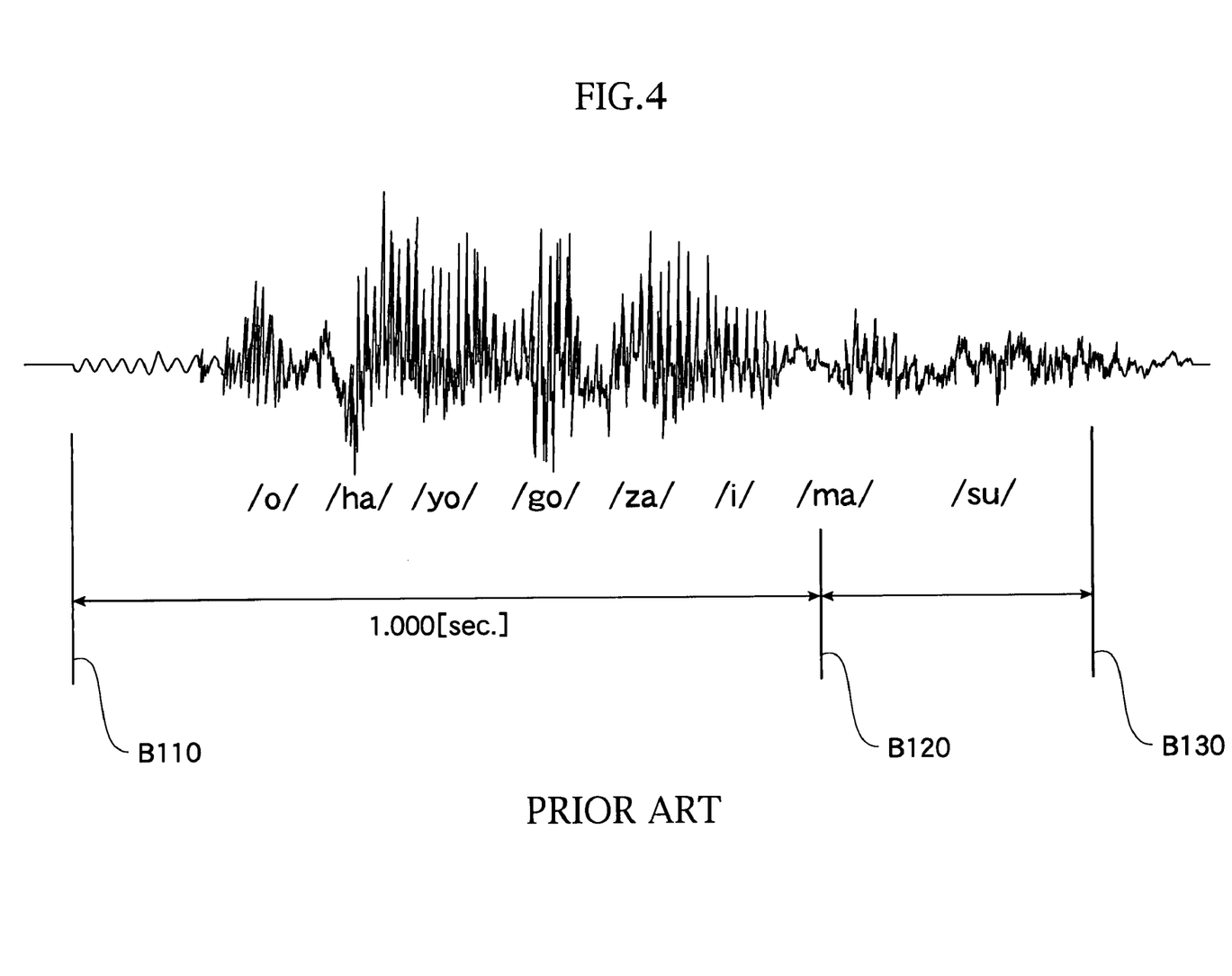
FIG. 4 is a diagram showing a conventional concept of acquiring a phoneme and an utterance time from voice data.

A difference between the invention apparatus and the conventional method is shown in FIGS. 3 and 4.

FIG. 3 is a diagram showing the concept of outputting a phoneme and utterance time on the basis of voice data in the method of the invention apparatus.

For example, when uttered voice data for outputting diagnosis data to be used in the chaos theoretical diagnosis is in the range of A110 to A130. The cutout start moment of diagnosis data is set to A110 where the utterance of an /o/ sound is not yet started. The cutout end moment of the diagnosis data is set to A120 where the utterance of a /yo/ sound has been finished. Accordingly, it becomes possible to output voice data ranging from A110 to A120 in the form of a phoneme or phoneme sequence as diagnosis data without being cut in the middle of a phoneme.

As a result, voice data can be output as diagnosis data in the form of a phoneme or phoneme sequence without being cut in the middle of a phoneme. Therefore, it also becomes possible to decrease the variation in diagnosis values, which exert influence on the value of the first Lyapunov exponent calculated by making a chaos theoretical diagnosis.

FIG. 4 is a diagram showing the concept of outputting a phoneme and utterance time on the basis of voice data in the conventional method.

For example, when voice data of an utterer for calculating diagnosis data to be used in the chaos theoretical diagnosis is in the range of B110 to B130. In the case where the time intervals to be processed of diagnosis data to be used in the chaos theoretical diagnosis is one second, the cutout start moment of diagnosis data is set to B110 and the cutout end moment of the diagnosis data is set to B120, which is a moment one second later than B110. Under these conditions, data between B110 and B120 is output as diagnosis data, and there is a possibility that the diagnosis data will be cut in the middle of a phoneme.

As a result, there is a possibility that the diagnosis data will be cut in the middle of a phoneme. Therefore, the variation occurs in diagnosis values, which exert influence on the value of the first Lyapunov exponent calculated by making a chaos theoretical diagnosis.

Figure 5:
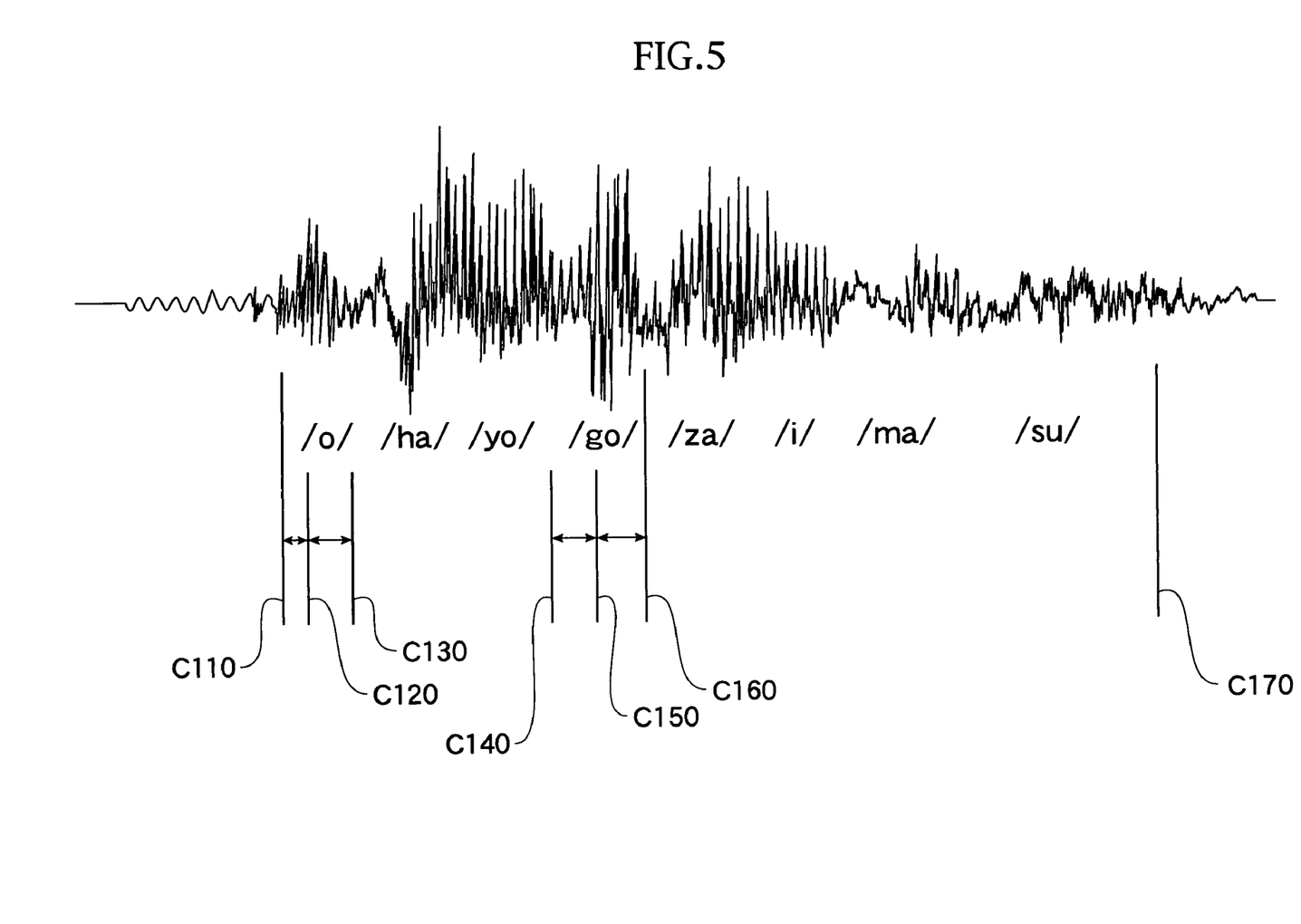
FIG. 5 is a diagram showing a concept of acquiring a phoneme and an utterance time from voice data in a preprocessing apparatus according to the embodiment of the present invention.

FIG. 5 is a diagram showing the concept of setting an offset when cutting out a phoneme in the invention apparatus.

For example, it is supposed that voice data of an utterer for outputting diagnosis data to be used in the chaos theoretical diagnosis is in the range of C110 to C170. The cutout start moment is set to C110 and the cutout end moment is set to C120. In order to prevent a phoneme from being cut in the middle of the phoneme, an offset value equal to or less than one phoneme is set for the cutout end moment C120 by offset providing means. Thus, the cutout end moment is shifted to C130, being able to prevent a phoneme from being cut in the middle of the phoneme.

Furthermore, when the cutout start moment is set to C150 and the cutout end moment is set to C160, and an offset value equal to or less than one phoneme is set for the cutout start moment C150 as a minus value by offset providing means. Thus, the cutout start moment is shifted to C140, being able to output diagnosis data containing voice data uttered before the diagnosis data.

INDUSTRIAL APPLICABILITY

The present invention relates to a preprocessing apparatus, which belongs to the field of medical diagnosis techniques, connected to an apparatus for diagnosing a psychosomatic state on the basis of a voice uttered by a human being, an apparatus for diagnosing a brain function, an apparatus for diagnosing a human factor, an apparatus for diagnosing affinity, and an apparatus for diagnosing a vocational aptitude. The present invention provides an industrially useful apparatus capable of reducing the variation in the first Lyapunov exponent calculated using a chaos theoretical diagnosis by cutting out unit voice data used in the chaos theoretical diagnosis while taking a phoneme as the unit, and capable of calculating a diagnosis value having a reliability equal to or higher than that obtained by using the conventional technique, on the basis of voice data shorter than that in the case using the conventional technique.

The invention claimed is:

1. A sensitivity enhancement apparatus to be connected to a chaos theoretical voice diagnosis apparatus for use as a preprocessing device, the sensitivity enhancement apparatus comprising:

a voice input apparatus for acquiring an uttered voice;

an analog-to-digital conversion apparatus for converting the acquired uttered voice to digital voice data;

a comparator for selecting, from the digital voice data, voice data having a first level greater than or equal to a certain level, and for outputting the selected digital voice data;

a voice data cutout apparatus capable of cutting out a phoneme unit of the selected digital voice data of a second level which is greater than or equal to the first level, and including an offset section for (i) providing a cutout start moment and a cutout end moment, according to which the cutout apparatus cuts out the phoneme unit and (ii) providing an offset value less than or equal to one phoneme; and a voice data output apparatus for outputting the phoneme unit cutout by the voice data cutout apparatus, wherein, when the cutout end moment is located at a middle of a phoneme of the phoneme unit cut out by the voice data cutout apparatus, the voice data cutout apparatus is operable to shift the cutout end moment to an end of the phoneme by shifting the cutout end moment by the offset value, and wherein, when the cutout start moment is located at a middle of a phoneme of the phoneme unit cut out by the voice data cutout apparatus, the voice data cutout apparatus is operable to shift the cutout start moment to a beginning of the phoneme by shifting the cutout start moment by the offset value.

2. The sensitivity enhancement apparatus according to claim 1, further comprising:

an internal memory for storing the selected digital voice data output from the comparator;

a phoneme database for storing phoneme data to be collated with the selected digital voice data stored in the internal memory; and a phoneme collation apparatus for cutting out, from the selected digital voice data stored in the internal memory, only a phoneme that coincides with the phoneme data stored in the phoneme database, wherein the internal memory, the phoneme database, and the phoneme collation apparatus are connected between the comparator and the voice data cutout apparatus.

3. The sensitivity enhancement apparatus according to claim 1, further comprising:

an internal memory for storing the selected digital voice data output from the comparator;

a phoneme sequence database for storing phoneme sequence data to be collated with the selected digital voice data stored in the internal memory; and a phoneme sequence collation apparatus for cutting out, from the selected digital voice data stored in the internal memory, only a phoneme sequence that coincides with the phoneme sequence data stored in the phoneme sequence database, wherein the internal memory, the phoneme sequence database, and the phoneme sequence collation apparatus are connected between the comparator and the voice data cutout apparatus.

4. The sensitivity enhancement apparatus according to claim 1, wherein the cutout start moment is located at a moment of an utterance of a preset vowel or a preset consonant, and the cutout end moment is located at a moment of an utterance at which at least one phoneme is finished, resulting in a cutout unit of digital voice data being formed by a phoneme or a phoneme sequence.

5. The sensitivity enhancement apparatus according to claim 1, wherein the voice data cutout apparatus includes a phoneme discrimination section for arbitrarily selecting and setting a specific phoneme or a specific phoneme sequence, and cuts out, from the selected digital voice data, a unit of digital voice data formed of a phoneme or a phoneme sequence that coincides with the specific phoneme or the phoneme sequence selected and set by the phoneme discrimination section.

* * * * *